(12) United States Patent
Schubert et al.

(10) Patent No.: US 8,501,150 B2
(45) Date of Patent: Aug. 6, 2013

(54) METAL OXIDES FROM METAL-ORGANIC FRAMEWORK MATERIALS

(75) Inventors: Markus Schubert, Ludwigshafen (DE); Ulrich Müller, Neustadt (DE); Natalia Trukhan, Ludwigshafen (DE)

(73) Assignees: BASF Aktiengesellschaft, Ludwigshafen (DE); BASF SE, Ludwigshafen (DE)

( * ) Notice: Subject to any disclaimer, the term of this patent is extended or adjusted under 35 U.S.C. 154(b) by 98 days.

(21) Appl. No.: 12/297,298

(22) PCT Filed: Apr. 12, 2007

(86) PCT No.: PCT/EP2007/053571
§ 371 (c)(1),
(2), (4) Date: Oct. 15, 2008

(87) PCT Pub. No.: WO2007/118843
PCT Pub. Date: Oct. 25, 2007

(65) Prior Publication Data
US 2009/0305040 A1    Dec. 10, 2009

(30) Foreign Application Priority Data

Apr. 18, 2006 (EP) .................................. 06112713

(51) Int. Cl.
*C01F 7/02* (2006.01)
*C01B 13/14* (2006.01)
(52) U.S. Cl.
USPC ...................................... 423/625; 423/592.1

(58) Field of Classification Search
USPC .............. 423/608, 610, 625, 626, 592.1, 609, 423/635, 636; 502/300–355
See application file for complete search history.

(56) References Cited

U.S. PATENT DOCUMENTS 3,908,002 A * 9/1975 Holler ............................ 423/628
4,146,504 A * 3/1979 Deffeyes ........................ 502/304
4,656,156 A   4/1987 Misra
4,778,671 A * 10/1988 Wusirika ..................... 423/592.1

(Continued)

FOREIGN PATENT DOCUMENTS

CA  2003320   5/1990
CA  2327097   10/1999

(Continued)

OTHER PUBLICATIONS

International Preliminary Report on Patentability of International Application No. PCT/EP2007053571 issued on Jul. 8, 2008.

(Continued)

*Primary Examiner* — Anthony J Zimmer
(74) *Attorney, Agent, or Firm* — Novak Druce Connolly Bove + Quigg LLP (57) ABSTRACT

The present invention relates to a method for producing a metal oxide by heating a porous metal-organic framework material, the framework material comprising at least one at least bidentate organic compound bound to at least one metal ion by coordination, and the metal ion being selected from the metals comprising groups 2 to 4 and 13 of the Periodic Table of the Elements, above the complete decomposition temperature of the framework material, and also to metal oxides obtainable by this method, and to the use thereof.

5 Claims, 3 Drawing Sheets

A                                   B

U.S. PATENT DOCUMENTS

| | | |
|---|---|---|
| 5,210,063 A | 5/1993 | Chopin et al. |
| 5,922,294 A | 7/1999 | Chattha et al. |
| 6,139,814 A | 10/2000 | Shigapov et al. |
| 2004/0065619 A1 | 4/2004 | Klabunde et al. |
| 2005/0239645 A1 | 10/2005 | Schuth et al. |

FOREIGN PATENT DOCUMENTS

| | | |
|---|---|---|
| DE | 10226131 | 12/2003 |
| EP | 0370728 | 5/1990 |
| EP | 0449672 | 10/1991 |
| EP | 1595847 | 11/2005 |
| WO | WO-99/50203 | 10/1999 |

OTHER PUBLICATIONS

C.Y Su et al., J. Am. Chem. Soc. 126, 2004, p. 3576-3586, Exceptionally Stable, Hollow Tubular Metal-Organic Architectures: Synthesis, Chracterization, and Solid-State Transformation Study.

\* cited by examiner

METAL OXIDES FROM METAL-ORGANIC FRAMEWORK MATERIALS

CROSS REFERENCE TO RELATED APPLICATIONS

This application is a 35 U.S.C. 371 National Stage Application of International Application No. PCT/EP2007/053571, filed Apr. 12, 2007, claiming priority from European Application No. 06112713.0, filed Apr. 18, 2006, the entire contents of which are incorporated herein by reference in their entireties.

The present invention relates to methods for producing metal oxides from porous metal-organic framework materials, metal oxides which are obtainable from these methods, and also use thereof.

Metal oxides are an interesting group of substances and are used for numerous applications.

Not least for this reason there exist in the prior art numerous methods for obtaining such metal oxides. In addition to their preparation, for example, from ores, large scale manufacture, in particular, of high-purity metal oxides, is a possibility.

Starting materials of such manufacturing methods can be of differing nature. For instance, α-aluminum oxide, for example, is produced from bauxite. $\gamma$-$Al_2O_3$, which is known for its porosity, can be manufactured, for example, from hydrargillite or boehmite, the $\beta$-$Al_2O_3$ being converted to $\alpha$-$Al_2O_3$ at a temperature above 1000° C. $\gamma$-$Al_2O_3$ serves, for example, as adsorbent, catalyst or catalyst support.

For the production of metal oxides, metal-organic compounds are also used. The metal oxides can in this case be manufactured, for example, using a chemical gas-phase deposition. As a result, in particular layers can be formed on corresponding substrates. Furthermore, sol-gel methods, freeze-drying or the production by flame pyrolysis are known.

An interesting approach for the manufacture of zinc oxide is described by C.-Y. Su et al., J. Am. Chem. Soc. 126 (2004), 3576-3586. In this case, first metal-organic framework materials are produced which first form a porous three-dimensional metal-organic framework from a metal ion (zinc) and an organic ligand (3-amino-1,2,4-triazole or 3-amino-1,2,4-triazole-5-carboxylic acid). Heating the framework material in an oxygen atmosphere, at temperatures above 600° C., leads to the formation of zinc oxide.

Porous metal-organic framework materials based on zinc are known in the literature and are distinguished by a comparatively high specific surface area, so that these materials are frequently proposed for carrying out, for example, adsorptions of gases. In this case, zinc terephthalate (MOF-5) is the most well known.

However, it is not known in the prior art whether the zinc oxide formed from a metal-organic framework material has properties which make the use of such an oxide appear promising.

An object of the present invention is thus to provide methods for producing metal oxides, and also such metal oxides, in order to supply these to a suitable application.

The object is achieved by a method for producing a metal oxide comprising the step
 heating a porous metal-organic framework material, the framework material comprising at least one at least bidentate organic compound bound to at least one metal ion by coordination, and the metal ion being selected from the metals comprising groups 2 to 4 and 13 of the Periodic Table of the Elements, above the complete decomposition temperature of the framework material.

The object is achieved in addition by a metal oxide obtainable by the inventive method.

This is because it has been found that the oxides of the abovementioned metals of groups 2 to 4 and 13 which are produced by the inventive method have a comparatively high specific surface area and thus are usable in particular in fields of use for the adsorption of substances. These specific surface areas which are comparatively high compared with the prior art might be explainable by the fact that the framework structure of the metal-organic framework material is at least in part retained in the structure of the corresponding metal oxide.

Surprisingly, however, it has been found that the prior art zinc oxide from a metal-organic framework material has very low specific surface areas and thus is not particularly suitable for being supplied to corresponding uses. It is therefore all the more surprising that this is possible using the inventive metals.

The inventive method for producing a metal oxide thus proceeds from a step in which the porous metal-organic framework material is heated.

In this step the material can be present in a dispersion or as a dry solid. In addition, the metal-organic framework material can be present as powder or as shaped body or both. Preferably, the heating proceeds using a porous metal-organic framework material in the form of a powder.

The heating can proceed by methods known to those skilled in the art. Typically, the heating proceeds in a furnace suitable therefor, such as, for example, a muffle furnace or rotary tubular kiln. When a furnace is used it is, in addition, expedient that possibilities exist for being able to carry out the heating in the presence of a suitable atmosphere. For this, accordingly, a feed for a corresponding gas or gas mixture can be mounted in or on the furnace in such a manner that the porous metal-organic framework material-comprising furnace chamber can be flooded with the corresponding gas or gas mixture.

The porous metal-organic framework material is heated as far as is required to convert the metal-organic framework material to the corresponding metal oxide. In this case, therefore, it is heated above the complete decomposition temperature of the metal-organic framework material.

For the purposes of the present invention, "complete decomposition temperature" is to be taken to mean that temperature at which the porous metal-organic framework material begins to convert into the corresponding metal oxide. However, it is likewise possible that the metal-organic framework material is converted to the metal oxide via intermediate stages. For example, before formation of the metal oxide, a carbonate might have been formed. In such a case, "complete decomposition temperature" is to be taken to mean the temperature which is required to convert the respective last intermediate stage to the metal oxide.

The complete decomposition temperature can be determined on the basis of methods known to those skilled in the art. For example, this temperature can be determined by thermogravimetry, detection of the formation of the corresponding metal oxide likewise being able to be carried out by accompanying analysis.

The complete decomposition temperature which is required to produce the corresponding metal oxide from a porous metal-organic framework material is typically in the range from 250° C. to 1000° C. Further preferably, the complete decomposition temperature is in a range from 350° C. to 800° C. Particularly preferably, the complete decomposition temperature is in the range from 450° C. to 650° C.

If the metal oxide is present in various modifications which can be obtained by temperature treatment, the thermally higher-level modification(s) can be obtained from the metal-organic framework material by applying the corresponding temperature stage, or the lower-level modification(s) is (are) obtained first, and in a further step the conversion to the desired modification can then proceed.

As has already been mentioned above, the porous metal-organic framework material can be heated in a suitable atmosphere. If the porous metal-organic framework material comprises at least one at least bidentate organic compound which itself has sufficient oxygen, it is not absolutely necessary that an oxygen-supplying substance be provided externally, in order to convert the porous metal-organic framework material into a metal oxide. Examples of such at least bidentate organic compounds which comprise oxygen are carboxylic acids, alcohols, ketones, aldehydes, ethers, esters and phenols. To this extent, the porous metal-organic framework material could be heated in a vacuum. Expediently, however, the heating is carried out under atmospheric conditions. In such a case, the heating of the porous metal-organic framework material could also take place in the presence of an inert atmosphere. Such atmospheres could be formed by gases such as nitrogen, noble gases such as helium or argon, and mixtures thereof. However, this is an exception.

Preferably, however, the porous metal-organic framework material is heated in the presence of an oxidizing atmosphere having an oxygen-supplying component. As a result it can be ensured that sufficient oxygen is available for converting the porous metal-organic framework material to the corresponding metal oxide. This can, in particular, also contribute to the abovementioned intermediate stages being "skipped". Such oxidizing atmospheres can be obtained by means of corresponding oxygen-supplying gases or gas mixtures. As the simplest and most preferred gas mixture, in this case, air may be mentioned, which usually comprises a sufficiently high fraction of molecular oxygen. If appropriate, the air can be used in enriched form with further oxygen. Finally, it is of course likewise possible that pure oxygen is used as oxidizing atmosphere. Furthermore, other gases or gas mixtures can also be used which, for example, are enriched with molecular oxygen. In this case, in particular inert gases would be preferred. For instance, suitable gas mixtures for producing an oxidizing atmosphere used on heating the porous metal-organic framework material can be helium, argon, nitrogen or mixtures thereof, in each case used enriched with oxygen.

The porous metal-organic framework material can be exposed to an oxidizing atmosphere in such a manner that during the heating the atmosphere is unchanged. The gas or gas mixture surrounding the porous metal-organic framework material is thus not exchanged, so that the oxygen-supplying component of the atmosphere decreases during heating.

In addition, it is possible to keep the atmosphere roughly constant during heating with respect to its oxygen-supplying component by replenishing at least this component.

However, preferably, the oxygen-supplying component is increased during heating. This can serve for temperature control of the exothermic reaction. A possible embodiment is that the atmosphere is exchanged for a gas or gas mixture having a higher fraction of oxygen-supplying component. This can take place, in particular, in such a manner that, after the start of heating, oxygen is supplied to the atmosphere until finally a defined oxygen atmosphere is present. The increase can take place stepwise or continuously.

The porous metal-organic framework material for the inventive method for producing a metal oxide must comprise the metal ion corresponding to the metal of the metal oxide. However, the porous metal-organic framework material can also comprise a plurality of metal ions. In this case, then, correspondingly a metal oxide is formed which likewise is made up of a plurality of metals.

In the event that a plurality of metal ions are present in the metal-organic framework material, at least one of these metal ions must be capable of binding the at least one at least bidentate organic compound by coordination in order to obtain the corresponding porous metal-organic framework material. If, in addition, one or more metals are present in ionic form, it or they likewise can be present in the structure of the metal-organic framework material by coordination to the at least one at least bidentate organic compounds or further at least bidentate organic compounds. In addition, however, it is likewise possible that this is not the case. Finally, in the event of presence of a plurality of metal ions, the ratio of the ions can be given in a stoichiometric ratio. In addition, a non-stoichiometric ratio may be present. In this context, it is then also possible to proceed from what is termed a doped porous metal-organic framework material. Such doped framework materials are described, for example, in German patent application number 10 2005 053 430.0 of the applicant. Such doped porous metal-organic framework materials are distinguished in that the distribution of the doping metal is random.

Furthermore, the porous metal-organic framework material can likewise be impregnated by a further metal, for example in the form of a salt. A method for impregnation is described, for example, in EP-A 1 070 538.

For the purposes of the present invention, two metal ions of one and the same metal of different oxidation state count as two different metal ions. In this case, therefore, a corresponding metal oxide can be obtained in which the metal is present in different oxidation states. Preferably, however, in particular in the presence of an oxidizing atmosphere, such a metal will be present as metal oxide solely in the highest stable oxidation state.

For the purposes of the present invention, it is preferred when the porous metal-organic framework material has solely one metal ion of one metal, in particular of one oxidation state.

The metal ion or metal ions are selected from the metals consisting of groups 2 to 4 and 13 of the Periodic Table of the Elements.

Particularly suitable metals of group 2 of the Periodic Table of the Elements are beryllium, magnesium, calcium, strontium and also barium.

Particularly suitable metals of group 3 of the Periodic Table of the Elements are scandium, yttrium, lanthanum and also the lanthanides.

Particularly suitable metals of group 4 of the Periodic Table of the Elements are titanium, zirconium and also hafnium.

Particularly suitable metals of group 13 of the Periodic Table of the Elements are aluminum, boron, gallium and also indium.

Further preferably, the metals are magnesium, calcium, strontium, barium, zirconium and also aluminum.

Very particularly preferably, the metal ion or metal ions is or are from the group of metals consisting of aluminum, magnesium and zirconium.

In the event that more than one metal ion is present in porous metal-organic framework materials, in particular aluminates of the formula $M^{I}AlO_2$ or $M^{II}Al_2O_4$ can be obtained, $M^{I}$ being a monovalent metal ion and $M^{II}$ being a divalent metal ion. In particular, spinels can be obtained.

In the event that the metal-organic framework material, in addition to titanium, comprises further metals, it is possible to obtain titanates, in particular ilmenite (FeTiO$_3$) but also MgTiO$_3$, MnTiO$_3$, FeTiO$_3$, CoTiO$_3$, NiTiO$_3$, CaTiO$_3$, SrTiO$_3$, BaTiO$_3$, Mg$_2$TiO$_4$, Zn$_2$TiO$_4$ and also Mn$_2$TiO$_4$.

When zirconium is used in the metal-organic framework material and, in addition, at least one further metal ion, corresponding zirconates can be obtained.

Suitable porous metal-organic framework materials are known from the prior art or can be produced in a similar manner on the basis of the methods described in the prior art. Metal-organic framework materials are described, for example, in U.S. Pat. No. 5,648,508, EP-A-0 790 253, M. O. Keeffe et al., J. Sol. State Chem., 152 (2000), pages 3 to 20, H. Li et al., Nature 402, (1999), page 276, M. Eddaoudi et al., Topics in Catalysis 9, (1999), pages 105 to 111, B. Chen et al., Science 291, (2001), pages 1021 to 1023, DE-A-101 11 230, WO-A 2005/049892 and A. C. Sudik et al., J. Am., Chem. Soc. 127 (2005), 7110 to 7118.

Porous metal-organic framework materials based on aluminum and magnesium are, in addition, described in particular in DE-A 10 2005 039 623, and also the literature cited therein.

Porous metal-organic framework materials based on zirconium and titanium are described, in particular, in the applicant's own European patent application having the attorney reference B06/0128EP which is submitted in parallel.

The term "at least bidentate organic compound" designates an organic compound which comprises at least one functional group which is capable of forming, to a given metal ion, at least two, preferably two, coordinate bonds, and/or, to two or more, preferably three metal atoms, in each case one coordinate bond.

As functional groups via which said coordinate bonds can be formed, in particular mention may be made, for example, of the following functional groups: —CO$_2$H, —CS$_2$H, —NO$_2$, —B(OH)$_2$, —SO$_3$H, —Si(OH)$_3$, —Ge(OH)$_3$, —Sn(OH)$_3$, —Si(SH)$_4$, —Ge(SH)$_4$, —Sn(SH)$_3$, PO$_3$H, —AsO$_4$H, —AsO$_4$H, —P(SH)$_3$, —As(SH)$_3$, —CH(RSH)$_2$, —C(RSH)$_3$—CH(RNH$_2$)$_2$—C(RNH$_2$)$_3$, —CH(ROH)$_2$, —C(ROH)$_3$, —CH(RCN)$_2$, —C(RCN)$_3$, where R is, for example, preferably an alkylene group having 1, 2, 3, 4 or 5 carbon atoms such as, for example, a methylene, ethylene, n-propylene, isopropylene, n-butylene, isobutylene, tert-butylene or n-pentylene group, or an aryl group comprising one or two aromatic nuclei such as, for example, 2 C$_6$ rings which if appropriate can be fused and independently of one another can be suitably substituted with at least in each case one substituent, and/or which independently of one another in each case can have at least one heteroatom, such as, for example, N, O and/or S. According to likewise preferred embodiments, functional groups may be mentioned in which the abovementioned radical R is not present. In this respect mention may be made of, inter alia, —CH(SH)$_2$, —C(SH)$_3$, —CH(NH$_2$)P, —C(NH$_2$)$_3$, —CH(OH)$_2$, —C(OH)$_3$, —CH(CN)$_2$ or —C(CN)$_3$.

The at least two functional groups can in principle be bound to any suitable organic compound provided it is ensured that this organic compound having functional groups is capable of forming the coordinate bond and of producing the framework material.

Preferably, the organic compounds which comprise the at least two functional groups are derived from a saturated or unsaturated aliphatic compound or an aromatic compound or a both aliphatic and aromatic compound.

The aliphatic compound or the aliphatic part of the both aliphatic and aromatic compound can be linear and/or branched and/or cyclic, a plurality of cycles per compound also being possible. Further preferably, the aliphatic compound or the aliphatic part of the both aliphatic and aromatic compound comprises 1 to 15, further preferably 1 to 14, further preferably 1 to 13, further preferably 1 to 12, further preferably 1 to 11, and particularly preferably 1 to 10 carbon atoms, such as, for example, 1, 2, 3, 4, 5, 6, 7, 8, 9 or 10 carbon atoms. Particular preference is given in this case to, inter alia, methane, adamantane, acetylene, ethylene or butadiene.

The aromatic compound or the aromatic part of the both aromatic and aliphatic compound can have one nucleus or else a plurality of nuclei such as, for example, two, three, four or five nuclei, the nuclei being able to be present separately from one another and/or at least two nuclei being able to be present in condensed form. Particularly preferably, the aromatic compound, or the aromatic part of the both aliphatic and aromatic compound has one, two or three nuclei, one or two nuclei being particularly preferred. Independently of one another, in addition, each nucleus of said compound can comprise at least one heteroatom such as, for example, N, O, S, B, P, Si, Al, preferably N, O and/or S. Further preferably, the aromatic compound or the aromatic part of the both aromatic and aliphatic compound comprises one or two C$_6$ nuclei, the two being present either separately from one another or in condensed form. In particular, as aromatic compounds, mention may be made of benzene, naphthalene and/or biphenyl and/or bipyridyl and/or pyridyl.

Particularly preferably, the at least bidentate organic compound is derived from a dicarboxylic, tricarboxylic, or tetracarboxylic acid or sulfur analogs thereof. Sulfur analogs are the functional groups —C(=O)SH and also tautomer thereof and C(=S)SH which may be used instead of one or more carboxylic acid groups.

The term "derive", for the purposes of the present invention, means that the at least bidentate organic compound can be present in the framework material in partly deprotonated or completely deprotonated form. In addition, the at least bidentate organic compound can comprise further substituents, such as, for example, —OH, —NH$_2$, —OCH$_3$ —CH$_3$, —NH (CH$_3$), —N(CH$_3$)$_2$, —CN and also halides.

For example, for the purposes of the present invention, mention may be made of dicarboxylic acids, for example oxalic acid, succinic acid, tartaric acid, 1,4-butanedicarboxylic acid, 4-oxopyran-2,6-dicarboxylic acid, 1,6-hexane-dicarboxylic acid, decanedicarboxylic acid, 1,8-heptadecanedicarboxylic acid, 1,9-heptadecanedicarboxylic acid, heptadecanedicarboxylic acid, acetylene-dicarboxylic acid, 1,2-benzenedicarboxylic acid, 2,3-pyridinedicarboxylic acid, pyridine-2,3-dicarboxylic acid, 1,3-butadiene-1,4-dicarboxylic acid, 1,4-benzenedicarboxylic acid, p-benzenedicarboxylic acid, imidazole-2,4-dicarboxylic acid, 2-methylquinoline-3,4-dicarboxylic acid, quinoline-2,4-dicarboxylic acid, quinoxaline-2,3-dicarboxylic acid, 6-chloroquinoxaline-2,3-dicarboxylic acid, 4,4'-diaminophenylmethane-3,3'-dicarboxylic acid, quinoline-3,4-dicarboxylic acid, 7-chloro-4-hydroxyquinoline-2,8-dicarboxylic acid, diimido-dicarboxylic acid, pyridine-2,6-dicarboxylic acid, 2-methylimidazole-4,5-dicarboxylic acid, thiophene-3,4-dicarboxylic acid, 2-isoproipylimidazole-4,5-dicarboxylic acid, tetrahydropyran-4,4-dicarboxylic acid, perylene-3,9-dicarboxylic acid, perylenedicarboxylic acid, Pluriol E 200-dicarboxylic acid, 3,6-dioxaoctane-dicarboxylic acid, 3,5-cyclohexadiene-1,2-dicarboxylic acid, octadicarboxylic acid, pentane-3,3-carboxylic acid, 4,4'-diamino-1,1'-diphenyl-3,3'-dicarboxylic acid, 4,4'-diaminodiphenyl-3,3'-dicarboxylic acid, benzidine-3,3'-dicarboxylic acid, 1,4-bis(phenylamino)benzene-2,5-dicarboxylic acid, 1,1'-dinaphthyl-5,5'-dicarboxylic acid, 7-chloro-8-methylquinoline-2,3-dicarboxylic acid, 1-anilinoanthraquinone-2,4'-dicarboxylic acid, polytetrahydrofuran-250-dicarboxylic acid, 1,4-bis(carboxymethyl)piperazine-2,3-dicarboxylic acid, 7-chloroquinoline-3,8-dicarboxylic acid, 1-(4-carboxy)phenyl-3-(4-chloro)phenylpyrazoline-4,5-dicarboxylic acid. 1,4,5,6,7,7-hexachloro-5-norbornene-2,3-dicarboxylic acid, phenylindanedicarboxylic acid, 1,3-dibenzyl-2-oxoimidazolidine-4,5-dicarboxylic acid, 1,4-cyclohexanedicarboxylic acid, naphthalene-1,8-dicarboxylic acid, 2-benzoylbenzene-1,3-dicarboxylic acid, 1,3-dibenzyl-2-oxoimidazolidine-4,5-cis-dicarboxylic acid, 2,2'-biquinoline-4,4'-dicarboxylic acid, pyridine-3,4-dicarboxylic acid, 3,6,9-trioxaundecanedicarboxylic acid, O-hydroxybenzophenonedicarboxylic acid, Pluriol E 300-dicarboxylic acid, Pluriol E 400-dicarboxylic acid, Pluriol E 600-dicarboxylic acid, pyrazole-3,4-dicarboxylic acid, 2,3-pyrazinedicarboxylic acid, 5,6-dimethyl-2,3-pyrazinedicarboxylic acid, 4,4'-diamino(diphenyl ether)-diimidodicarboxylic acid, 4,4'-diaminodiphenylmethanediimidodicarboxylic acid, 4,4'-diamino(diphenyl sulfone)diimidedicarboxylic acid, 2,6-naphthalene-dicarboxylic acid, 1,3-adamantanedicarboxylic acid, 1,8-naphthalenedicarboxylic acid, 2,3-naphthalenedicarboxylic acid, 8-methoxy-2,3-naphthalenedicarboxylic acid, 8-nitro-2,3-naphthalenedicarboxylic acid, 8-sulfo-2,3-naphthalenedicarboxylic acid, anthracene-2,3-dicarboxylic acid, 2',3'-diphenyl-p-terphenyl-4,4"-dicarboxylic acid, (diphenyl ether)-4,4'-dicarboxylic acid, imidazole-4,5-dicarboxylic acid, 4(1H)-oxothiochromene-2,8-dicarboxylic acid, 5-tert-butyl-1,3-benzenedicarboxylic acid, 7,8-quinolinedicarboxylic acid, 4,5-imidazole-dicarboxylic acid, 4-cyclohexene-1,2-dicarboxylic acid, hexatriacontanedicarboxylic acid, tetradecanedicarboxylic acid, 1,7-heptane-dicarboxylic acid, 5-hydroxy-1,3-benzenedicarboxylic acid, pyrazine-2,3-dicarboxylic acid, furan-2,5-dicarboxylic acid, 1-nonene-6,9-dicarboxylic acid, eicosenedicarboxylic acid, 4,4'-dihydroxydiphenylmethane-3,3'-dicarboxylic acid, 1-amino-4-methyl-9,10-dioxo-9,10-dihydroanthracene-2,3-dicarboxylic acid, 2,5-pyridinedicarboxylic acid, cyclohexene-2,3-dicarboxylic acid, 2,9-dichlorofluorubin-4,11-dicarboxylic acid, 7-chloro-3-methylquinoline-6,8-dicarboxylic acid, 2,4-dichlorobenzophenone-2',5'-dicarboxylic acid, 1,3-benzenedicarboxylic acid, 2,6-pyridinedicarboxylic acid, 1-methylpyrrole-3,4-dicarboxylic acid, 1-benzyl-1H-pyrrole-3,4-dicarboxylic acid, anthraquinone-1,5-dicarboxylic acid, 3,5-pyrazoledicarboxylic acid, 2-nitrobenzene-1,4-dicarboxylic acid, heptane-1,7-dicarboxylic acid, cyclobutane-1,1-dicarboxylic acid, 1,14-tetradecanedicarboxylic acid, 5,6-dehydronorbornane-2,3-dicarboxylic acid or 5-ethyl-2,3-pyridinedicarboxylic acid, tricarboxylic acids such as 2-hydroxy-1,2,3-propanetricarboxylic acid, 7-chloro-2,3,8-quinolinetricarboxylic acid, 1,2,4-benzenetricarboxylic acid, 1,2,4-butanetricarboxylic acid, 2-phosphono-1,2,4-butanetricarboxylic acid, 1,3,5-benzenetricarboxylic acid, 1-hydroxy-1,2,3-propanetricarboxylic acid, 4,5-dihydro-4,5-dioxo-1H-pyrrolo[2,3-F]quinoline-2,7,9-tricarboxylic acid, 5-acetyl-3-amino-6-methyl-benzene-1,2,4-tricarboxylic acid, 3-amino-5-benzoyl-6-methylbenzene-1,2,4-tricarboxylic acid, 1,2,3-propanetricarboxylic acid or aurintricarboxylic acid, or tetracarboxylic acids such as 1,1-dioxidoperylo[1,12-BCD]thiophene-3,4,9,10-tetracarboxylic acid, perylene-tetracarboxylic acids such as perylene-3,4,9,10-tetracarboxylic acid or perylene-1,12-sulfone-3,4,9,10-tetracarboxylic acid, butanetetracarboxylic acids such as 1,2,3,4-butanetetracarboxylic acid or meso-1,2,3,4-butanetetracarboxylic acid, decane-2,4,6,8-tetracarboxylic acid, 1,4,7,10,13,16-hexaoxacyclooctadecane-2,3,11,12-tetracarboxylic acid, 1,2,4,5-benzenetetracarboxylic acid, 1,2,11,12-dodecanetetracarboxylic acid, 1,2,5,6-hexanetetracarboxylic acid, 1,2,7,8-octane-tetracarboxylic acid, 1,4,5,8-naphthalenetetracarboxylic acid, 1,2,9,10-decanetetracarboxylic acid, benzophenonetetracarboxylic acid, 3,3',4,4'-benzo-phenorietetracarboxylic acid, tetrahydrofurantetracarboxylic acid or cyclopentane-tetracarboxylic acids such as cyclopentane-1,2,3,4-tetracarboxylic acid.

Very particular preference is given to using optionally at least monosubstituted aromatic dicarboxylic, tricarboxylic or tetracarboxylic acids having one, two, three, four or more rings, with each of the rings being able to comprise at least one heteroatom and two or more rings being able to comprise identical or different heteroatoms. Examples of preferred carboxylic acids of this type are one-ring dicarboxylic acids, one-ring tricarboxylic acids, one-ring tetracarboxylic acids, two-ring dicarboxylic acids, two-ring tricarboxylic acids, two-ring tetracarboxylic acids, three-ring dicarboxylic acids, three-ring tricarboxylic acids, three-ring tetracarboxylic acids, four-ring dicarboxylic acids, four-ring tricarboxylic acids and/or four-ring tetracarboxylic acids. Suitable heteroatoms are, for example, N, O, S, B, P, Si, Al, and preferred heteroatoms are N, S and/or O, Suitable substituents in this context are, inter alia, —OH, a nitro group, an amino group or an alkyl or alkoxy group.

Particularly preferably, as at least bidentate organic compounds, use is made of acetylenedicarboxylic acid (ADC), benzenedicarboxylic acids, naphthalene-dicarboxylic acids, biphenyldicarboxylic acids such as, for example, 4,4'-biphenyldicarboxylic acid (BPDC), bipyridinedicarboxylic acids such as, for example, 2,2'-bipyridinedicarboxylic acids such as, for example, 2,2'-bipyridine-5,5'-dicarboxylic acid, benzenetricarboxylic acids such as, for example, 1,2,3-benzenetricarboxylic acid or 1,3,5-benzenetricarboxylic acid (BTC), adamantanetetracarboxylic acid (ATC), adamantanedibenzoate (ADB), benzene-tribenzoate (BTB), methanetetrabenzoate (MTB), adamantanetetrabenzoate, or dihydroxyterephthalic acids such as, for example, 2,5-dihydroxyterephthalic acid (DHBDC).

Very particularly preferably, use is made of, inter alia, isophthalic acid, terephthalic acid, 2,5-dihydroxyterephthalic acid, 1,2,3-benzenetricarboxylic acid, 1,2,4-benzenetricarboxylic acid, 1,3,5-benzenetricarboxylic acid, fumaric acid, succinic acid, maleic acid, glutaric acid, 2,6-naphthalenedicarboxylic acid, 1,2,4,5-benzenetetracarboxylic acid, citric acid, tartaric acid or oxalic acid. Particular preference is given to oxalic acid, isophthalic acid, or terephthalic acid.

It is preferred when the at least one at least bidentate organic compound is made up only of the elements carbon, hydrogen and oxygen. It is preferred in this case that the molar ratio C:O is $\leq 3$, more preferably $\leq 2$.

In addition to these at least bidentate organic compounds, the MOF can also comprise one or more monodentate ligands.

Suitable solvents for producing the MOF are, inter alia, ethanol, dimethylformamide toluene, methanol, chlorobenzene, diethylformamide, dimethyl sulfoxide, water, hydrogen peroxide, methylamine, sodium hydroxide solution, N-methylpolidone ether, acetonitrile, benzyl chloride, triethylamine, ethylene glycol and mixtures thereof. Further metal ions, at least bidentate organic compounds and solvents for producing MOF are described, inter alia, in U.S. Pat. No. 5,648,508 or DE-A 101 11 230.

The inventive metal-organic framework materials for the process according to the invention comprise pores, in particular micro- and/or mesopores. Micropores are defined as those having a diameter of 2 nm or less and mesopores are defined by a diameter in the range from 2 to 50 nm, in each case in accordance with the definition as given in Pure Applied Chem. 57 (1985), pages 603-619, in particular on page 606. The presence of micro- and/or mesopores can be investigated using sorption measurements, these measurements determining the uptake capacity of the metal-organic framework materials for nitrogen at 77 kelvin as specified in DIN 66131 and/or DIN 66134.

Preferably, the specific surface area, calculated by the Langmuir model (DIN 66131, 66134), of an MOF in powder form is greater than 5 $m^2/g$, more preferably greater than 10 $m^2/g$, more preferably greater than 50 $m^2/g$, further more preferably greater than 500 $m^2/g$, further more preferably greater than 1000 $m^2/g$, and particularly preferably greater than 1500 $m^2/g$.

Shaped bodies made of metal-organic framework materials can have a lower specific surface area; preferably, however; greater than 10 $m^2/g$, more preferably greater than 50 $m^2/g$, further more preferably greater than 500 $m^2/g$, in particular greater than 1000 $m^2/g$.

The pore size of the porous metal-organic framework material can be controlled by selection of the suitable ligand and/or the at least bidentate organic compound. In general it is true that the larger the organic compound, the greater is the pore size. Preferably, the pore size is from 0.2 nm to 30 nm, particularly preferably the pore size is in the range from 0.3 nm to 3 nm, based on the crystalline material.

In a shaped body of the metal-organic framework material, however, larger pores occur, the pore size distribution of which can vary. Preferably, however, more than 50% of the total pore volume, in particular more than 75%, of pores are formed having a pore diameter of up to 1000 nm. Preferably, however, a majority of the pore volume is formed by pores from two diameter ranges. It is therefore further preferred when more than 25% of the total pore volume, in particular more than 50% of the total pore volume, is formed by pores which are in a diameter range from 100 nm to 800 nm, and when more than 15% of the total pore volume, in particular more than 25% of the total pore volume, is formed by pores which are in a diameter range of up to 10 nm. The pore size distribution can be determined by means of mercury porosimetry.

The production of shaped bodies from metal-organic framework materials is described, for example, in WO-A 03/102000.

The present invention further relates to a metal oxide obtainable from the inventive method for producing this metal oxide.

On account of the fact that porous metal-organic framework materials are used as precursor for the corresponding metal oxides and in this case at least in part the framework structure of the metal-organic framework material is reflected in the oxide and likewise in part, compared with the corresponding metal oxides in the prior art, give higher specific surface areas, the metal oxides obtainable by the inventive method are to be considered as novel substances.

Since the framework structure is at least in part retained, it is preferred when, and if this is the case, the specific surface area ($N_2$ according to Langmuir) of metal-organic framework material to oxide is preferably <50:1, particularly preferably <20:1, further particularly preferably <15:1, and in the case of metal-organic framework materials from main group metals, in particular <5:1 and further more preferably <4:1.

In the event that the metal oxide is $Al_2O_3$, it is preferred when the specific surface area is at least 400 $m^2/g$ ($N_2$ according to Langmuir).

In the event that the metal oxide is MgO, it is preferred when its specific surface area is at least 100 $m^2/g$ ($N_2$ according to Langmuir).

In the event that the metal oxide is $ZrO_2$, it is preferred when its specific surface area is at least 50 $m^2/g$ ($N_2$ according to Langmuir).

The metal oxides can each be present in the form in which the metal-organic framework material is used. Preferably, the metal-organic framework material is used as powder.

The inventive metal oxides differ from conventionally produced metal oxides, in particular, by their special morphology. Consequently, the inventive metal oxides can have improved properties for certain applications. In this case, likewise the pore radius distribution differing from metal oxides from known production methods, which usually corresponds to that of the framework material, is to be noted, which can cause an altered behavior in adsorption and separation methods. In addition, the simple production of doped metal oxides is possible. Finally, production from highly concentrated dispersions is possible.

The inventive metal oxides which are obtainable by the inventive method can in principle be used for all applications which are known for conventionally obtained metal oxides.

In particular, applications of interest are those in which a specific surface area as high as possible is advantageous.

Examples of uses of an inventive metal oxide are those where the metal oxide is used as ceramic material, as catalyst, in particular photocatalyst, pigment, for example light-protection pigment, support, for example as catalyst support, adsorbent, for example for storage or separation of substances, in particular of liquids or gases, as insulation material, abrasive, aid or filler.

EXAMPLES

Example 1

Production of Aluminum Oxide 23.9 kg of terephthalic acid (BDC) and 28 kg of $Al_2(SO_4)_3 \cdot 18H_2O$ are suspended in 150 kg of DMF and the mixture is stirred at 130° C. for 24 hours. The solid is then filtered off, washed with 4×10 kg of methanol and stripped dry using $N_2$ in the course of 96 hours.

This gives a surface area (determined by $N_2$ according to Langmuir) of 1381 $m^2/g$.

The resultant framework material in the form of a powder is calcined for approximately 24 h in a muffle furnace at about 475 to 500° C. in an air atmosphere. In this case the carbon is virtually quantitatively removed (residual content 0.35% by weight). The product is an amorphous aluminum oxide having an $N_2$ surface area of 452 $m^2/g$ (Langmuir).

Figure 1:
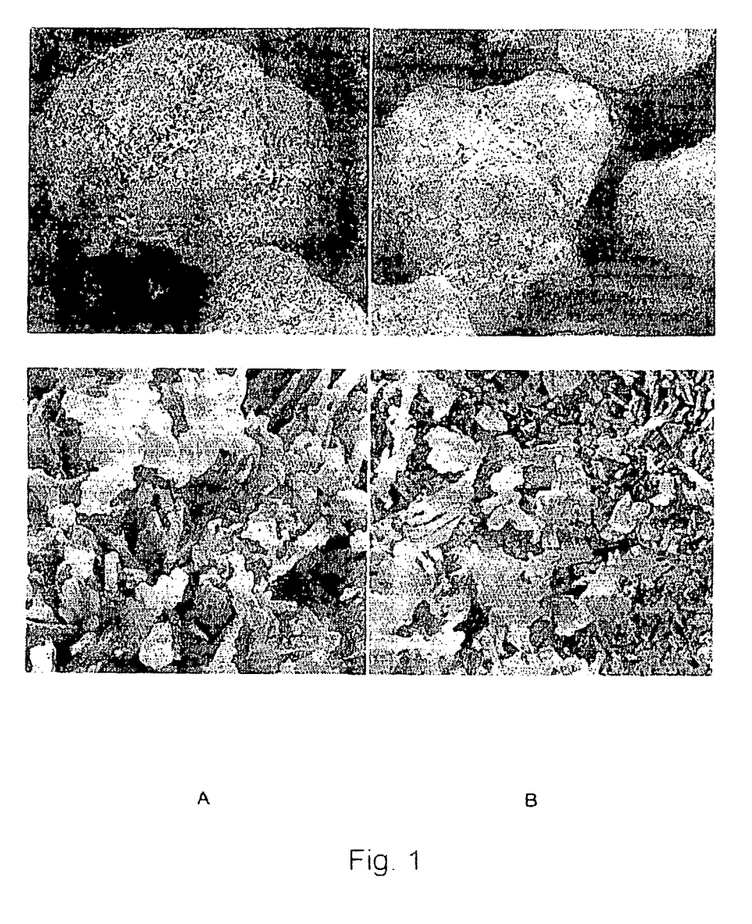

FIG. 1 shows the electron micrograph (SEM) of the metal-organic framework material (A) and the oxide (B), a scale of 1000:1 being used in the top half of the picture and a scale of 20 000:1 being used in the bottom half. As shown in FIG. 1, the morphology of the original particles is substantially retained.

Comparative Example 2

In comparison with example 1, the specific surface area of conventionally produced and commercially available aluminum oxide is determined. In this comparison, for the samples Versal 200 (UOP LLC, Des Plaines, US), Spheralite (Procatalyse, Usine de Salindre, FR), $Al_2O_3$ from Alcoa Inc. (Pittsburgh, US), Versal 250 (Eurosupport, KH Amersfoort, NL), a value for the specific surface area was found in the range from about 320 to 350 m²/g.

Example 3

Production of Magnesium Oxide 10.984 g of magnesium nitrate.6($H_2O$) are dissolved in 68.5 g of DEF, in an autoclave beaker (Teflon liner), 6.657 g of 2,6-naphthalenedicarboxylic acid are suspended in 68.5 g of DEF. Subsequently, the magnesium salt-comprising solution is added and the mixture is stirred for 10 min. The synthesis proceeds subsequently in the closed autoclave at 105° C. in the course of 24 hours. The yellow crystals are filtered off. The filtercake is slurried with 250 ml of DMF and stirred for 20 min. The product is filtered off, then first washed with DMF and subsequently with chloroform. Subsequently the product is dried in air.

The $N_2$ surface area (according to Langmuir) of an Mg-naphthalenedicarboxylic acid-MOF produced in this manner is typically in the range from 80 to 120 m²/g.

The magnesium-2,6-naphthalenedicarboxylic acid-MOF is calcined at 650° C. for 5 hours. The product is a magnesium oxide having an $N_2$ surface area of 133 m²/g (Langmuir).

Figure 2:
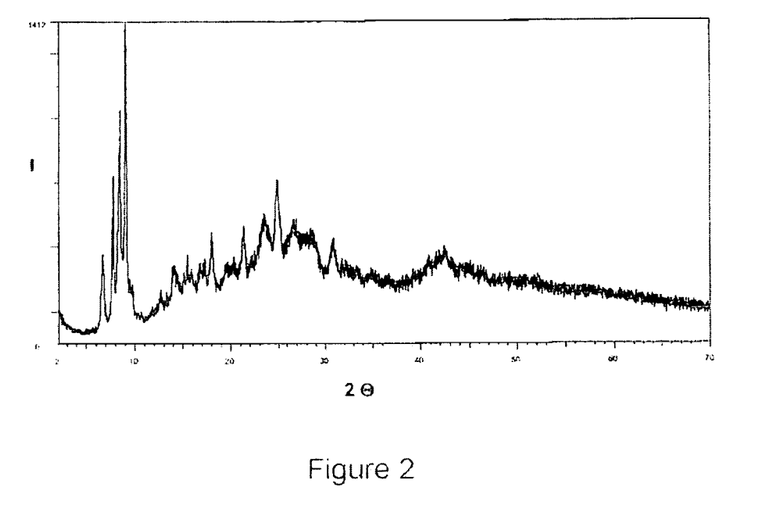
Figure 3:
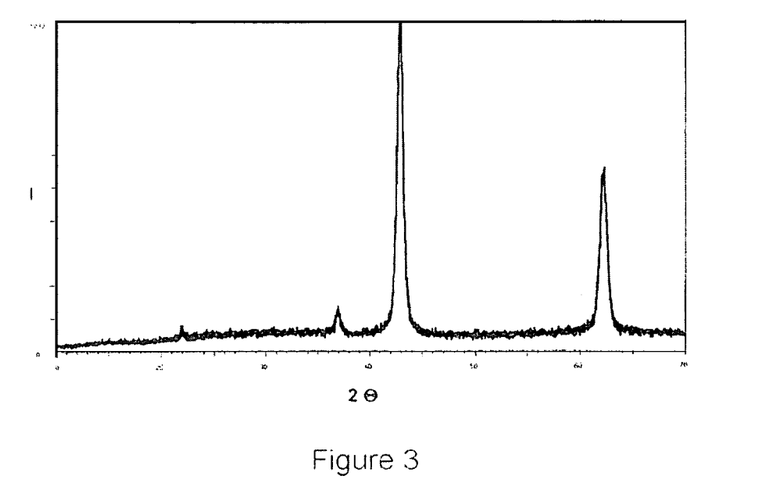

FIGS. 2 and 3 show the X-ray diffractogram (XRD) of framework material (FIG. 2) and oxide (FIG. 3), I showing the intensity (Lin (counts)) and 2 θ describes the 2-theta scale.

The morphology of the original particles is likewise substantially retained.

Example 4

Production of Zirconium Oxide 5 g of $ZrOCl_2$ and 9.33 g of terephthalic acid are stirred in 300 ml of DMF in a glass flask for 17 h at 130° C. under reflux. The precipitate is filtered off, washed with 3×50 ml of DMF and 4×50 ml of methanol and predried at 150° C. for 4 days in a vacuum drying cabinet. Subsequently, the product is calcined for 2 days in a muffle furnace at 275° C. (100 l/h of air). 5.17 g of a brown material are obtained.

This gives an $N_2$ surface area of 836 m²/g (Langmuir). The product is calcined at 500° C. for 48 h.

The product is a zirconium oxide having an $N_2$ surface area of 61 m²/g (Langmuir). The distribution of the pore diameters is essentially retained.

Example 5

Production of a Mixed Al/Zr Oxide

A Zr-doped Al-terephthalic acid-MOF is produced from 5 g of $AlCl_3.6H_2O$, 2.25 g of $ZrOCl_2$ and 8.14 g of terephthalic acid by precipitation in 300 ml of DMF (130° C., 17 h). After filtration and washing with DMF and methanol, this is first predried at 150° C. in a vacuum drying cabinet and subsequently calcined at 330° C. for 48 h in a muffle furnace with air feed. The MOF has an $N_2$ surface area of 1448 m²/g (Langmuir) and, in addition to 8.5% by weight of Al, also comprises 9.8% by weight of Zr.

The MOF precursor is calcined at 500° C. for 48 h and converted by this means into a mixed Al/Zr oxide. The product has a Langmuir surface area of 358 m²/g.

Comparative Example 6

Production of Zinc Oxide 96.7 g of $Zn(NOi)_2.4H_2O$ and 20.8 g of terephthalic acid are suspended in 2825 g of DEF. The reaction mixture is kept at 130° C. for 3.5 hours. After cooling, the solid is filtered off and washed with 4×500 ml of anhydrous acetone. The solid is first predried at room temperature in a nitrogen stream for 2 to 4 days and subsequently evacuated in a vacuum drying cabinet for 16 hours ($\leq$1 mbar).

The zinc-terephthalic acid-MOF (MOF-5) has an $N_2$ surface area of 2811 m²/g (Langmuir).

Figure 4:
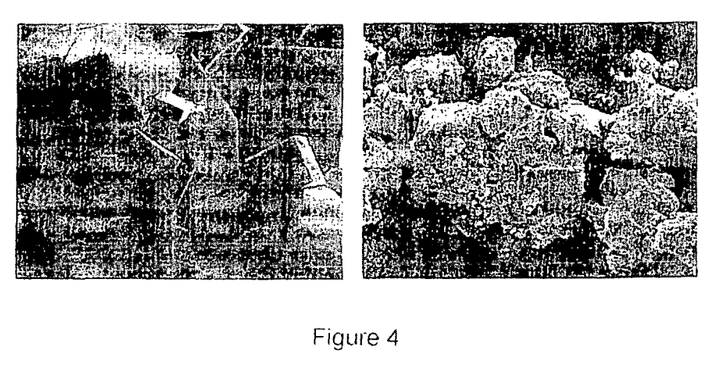

The resultant powder is calcined at 500° C. for 16 h. The product is a zinc oxide having an $N_2$ surface area of only 20 m²/g (Langmuir). FIG. 4 shows the electron micrograph (SEM) of MOF-5 (left) and oxide (right) at a resolution of 500:1. It can be seen that the MOF structure has mostly decomposed.

Example 7

Production of an Aluminum Oxide 27.8 g of $Al(NO_3)_3.9H_2O$ and 4.3 g of fumaric acid are suspended in 520.5 g of DMF and stirred for 3 days at 130° C. in a glass flask. The product is filtered off and rinsed with 2×100 ml of DMF and 4×100 ml of MeOH. 4.5 g of an Al-fumaric acid-MOF having an $N_2$ surface area of 776 m²/g (Langmuir) are obtained. After heating in air at 500° C., an aluminum oxide having a surface area of 510 m²/g is obtained.

The invention claimed is:

1. A method for producing a metal oxide comprising:
   creating a porous metal-organic framework by mixing in a solvent at least one bidentate organic compound derived from a dicarboxylic acid and a source of metal ions comprising aluminum, wherein the solvent is a dimethylformamide or a diethylformamide and wherein the bidentate organic compound is bound to the metal ion by coordination in the resulting porous metal-organic framework; and
   heating the porous metal-organic framework material above the complete decomposition temperature of the framework material.

2. The method according to claim 1, wherein the framework material contains only one metal, or is in doped form.

3. The method according to claim 1, wherein the heating proceeds in the presence of an oxidizing atmosphere having an oxygen-supplying component.

4. The method according to claim 3, wherein the concentration of the oxygen-supplying component is increased during heating.

5. The method according to claim 1, wherein the complete decomposition temperature is in the range from 250° C. to 1000° C.

* * * * *